(12) United States Patent
Sikiric

(10) Patent No.: US 10,350,293 B2
(45) Date of Patent: Jul. 16, 2019

(54) COMPOSITIONS AND METHODS FOR TREATING SYMPTOMS ASSOCIATED WITH MULTIPLE SCLEROSIS

(71) Applicant: Pharmacotherapia d.o.o., Split (HR)

(72) Inventor: Predrag Sikiric, Zagreb (HR)

(73) Assignee: Pharmacotherapia d.o.o., Split (HR)

( * ) Notice: Subject to any disclaimer, the term of this patent is extended or adjusted under 35 U.S.C. 154(b) by 0 days.

(21) Appl. No.: 15/676,405

(22) Filed: Aug. 14, 2017

(65) Prior Publication Data

US 2018/0055937 A1 Mar. 1, 2018

Related U.S. Application Data

(60) Provisional application No. 62/378,369, filed on Aug. 23, 2016.

(51) Int. Cl.
| | | |
|---|---|---|
| *A61K 9/08* | (2006.01) | |
| *A61K 9/14* | (2006.01) | |
| *A61K 38/02* | (2006.01) | |
| *A61K 47/10* | (2017.01) | |
| *A61K 9/00* | (2006.01) | |
| *A61K 9/20* | (2006.01) | |
| *A61K 38/10* | (2006.01) | |

(52) U.S. Cl.
CPC ............ *A61K 47/10* (2013.01); *A61K 9/0053* (2013.01); *A61K 9/08* (2013.01); *A61K 9/14* (2013.01); *A61K 9/20* (2013.01); *A61K 9/2018* (2013.01); *A61K 38/02* (2013.01); *A61K 38/10* (2013.01)

(58) Field of Classification Search
None
See application file for complete search history.

(56) References Cited

U.S. PATENT DOCUMENTS

| | | | | |
|---|---|---|---|---|
| 5,288,708 | A * | 2/1994 | Sikiric ............... | C07K 14/47 530/344 |
| 6,288,028 | B1 * | 9/2001 | Sikiric ............... | C07K 14/47 514/23 |

FOREIGN PATENT DOCUMENTS

| | | |
|---|---|---|
| WO | 92004368 | 3/1992 |
| WO | 9852973 | 11/1998 |
| WO | 2014142765 | 9/2014 |

OTHER PUBLICATIONS

Avila, et al., "Menstrual Cycle, menopause and pregnancy in patients with multiple sclerosis. How these affect the symptoms of disease" Baylor College of Medicine, poster. https://www.bcm.edu/neurology/pdf/poster_msc_FemaleHormones_congress.pdf, retrieved from the internet Nov. 14, 2017.

Balenovic, et al., "Inhibition of methyldigoxin-induced arrhythmias by pentadecapeptide BPC 157: a relation with NO-system" Regul Pept., 156(1-3):83-9 (2009).

Baric, et al., "Stable gastric pentadecapeptide BPC 157 heals rectovaginal fistula in rats" Life Sci., 148:63-70 (2016).

Barisic, et al., "Mortal hyperkalemia disturbances in rats are NO-system related. The life saving effect of pentadecapeptide BPC 157" Regul Pept., 181:50-66 (2013).

Bedekovic, et al., "Different effect of antiulcer agents on rat cysteamine-induced duodenal ulcer after sialoadenectomy, but not gastrectomy" Eur J Pharmacol., 477(1):73-80 (2003).

Bilic, et al., "The stable gastric pentadecapeptide BPC 157, given locally, improves CO2 laser healing in mice" Burns. 31(3):310-5 (2005).

Blagaic, et al., "Gastric pentadecapeptide BPC 157 counteracts morphine-induced analgesia in mice" J Physiol Pharmacol., 60 Suppl 7:177-81 (2009).

Blagaic, et al., "Gastric pentadecapeptide BPC 157 effective against serotonin syndrome in rats" Eur J Pharmacol., 512(2-3):173-9 (2005).

Blagaic, et al., "The influence of gastric pentadecapeptide BPC 157 on acute and chronic ethanol administration in mice" Eur J Pharmacol., 499(3):285-90 (2004).

Boban-Blagaic, et al., "The influence of gastric pentadecapeptide BPC 157 on acute and chronic ethanol administration in mice. The effect of N(G)-nitro-L-arginine methyl ester and L-arginine" Med Sci Monit., 12(1):BR36-45 (2006).

Brcic, et al., "Modulatory effect of gastric pentadecapeptide BPC 157 on angiogenesis in muscle and tendon healing" J Physiol Pharmacol., 60 Suppl 7:191-6 (2009).

(Continued)

*Primary Examiner* — John D Ulm
(74) *Attorney, Agent, or Firm* — Pabst Patent Group LLP

(57) ABSTRACT

Compositions and methods for treating one or more symptoms one or more symptoms such as reduced sexual desire and fecal compaction are provided. Accordingly, the disclosed composition can be administered to subjects in need thereof, including patients with multiple sclerosis, particularly in patients in which multiple sclerosis symptoms are exacerbated in the premenstrual time period/during the menstrual period.

The compositions are unit dosage forms including pharmaceutically acceptable salts of a BPC peptide. The unit dosage forms can be formulated for enteral, parenteral, or topical administration.

Also provided herein are methods of increasing sexual desire or reducing fecal compaction in a subject in need thereof. In one embodiment, the compositions disclosed herein are used to alleviate one or more symptoms in patients with multiple sclerosis, particularly in patients in which multiple sclerosis symptoms are exacerbated in the premenstrual time period.

The disclosed dosage forms can be administered orally or parenterally.

20 Claims, No Drawings
Specification includes a Sequence Listing.

(56) References Cited

OTHER PUBLICATIONS

Cerovecki, et al., "Pentadecapeptide BPC 157 (PL 14736) improves ligament healing in the rat" J Orthop Res., 28(9):1155-61 (2010).
Cesarec, et al., "Pentadecapeptide BPC 157 and the esophagocutaneous fistula healing therapy" Eur J Pharmacol., 701(1-3):203-12 (2013).
Clinical Trials NCT02637284, "PCO-02 Safety and Pharmacokinetics," trial, 6 pages, first appeared Dec. 22, 2015, last updated Dec. 22, 2015.
Dobric, et al., "Prolonged esophagitis after primary dysfunction of the pyloric sphincter in the rat and therapeutic potential of the gastric pentadecapeptide BPC 157" J Pharmacol Sci., 104(1):7-18 (2007).
Duplancic, et al., "Pentadecapeptide BPC 157 and anaphylactoid reaction in rats and mice after intravenous dextran and white egg administration" Eur J Pharmacol., 727:75-9 (2014).
Duvnjak, et al., "Assessment of value of pancreatic pseudocyst amylase concentration in the treatment of pancreatic pseudocysts by percutaneous evacuation" J Clin Ultrasound, 20(3):183-6 (1992).
Duvnjak, et al., "The value of pancreatic pseudocyst amylase concentration in the detection of pseudocyst communication with the pancreatic duct" Am J Gastroenterol. 86(5):595-8 (1991).
Gjurasin, et al., "Peptide therapy with pentadecapeptide BPC 157 in traumatic nerve injury" Regul Pept., 160(1-3):33-41 (2010).
Grabarevic, et al., "The influence of BPC 157 on nitric oxide agonist and antagonist induced lesions in broiler chicks" J Physiol Paris., 91(3-5):139-49 (1997).
Hrelec, et al., "Abdominal aorta anastomosis in rats and stable gastric pentadecapeptide BPC 157, prophylaxis and therapy" J Physiol Pharmacol.,60 Suppl 7:161-5 (2009).
Ilic, et al., "High hepatotoxic dose of paracetamol produces generalized convulsions and brain damage in rats. A counteraction with the stable gastric pentadecapeptide BPC 157 (PL 14736)" J Physiol Pharmacol.,61 (2):241-50 (2010).
Ilic, et al., "Ibuprofen hepatic encephalopathy, hepatomegaly, gastric lesion and gastric pentadecapeptide BPC 157 in rats" Eur J Pharmacol., 667(1-3):322-9 (2011b).
Ilic, et al., "Over-dose insulin and stable gastric pentadecapeptide BPC 157. Attenuated gastric ulcers, seizures, brain lesions, hepatomegaly, fatty liver, breakdown of liver glycogen, profound hypoglycemia and calcification in rats" J Physiol Pharmacol., 60 Suppl 7:107-14 (2009).
Ilic, et al., "Pentadecapeptide BPC 157 and its effects on a NSAID toxicity model: diclofenac-induced gastrointestinal, liver, and encephalopathy lesions" Life Sci., 88(11-12):535-42 (2011a).
Jandric, et al., "Salutary effect of gastric pentadecapeptide BPC 157 in two different stress urinary incontinence models in female rats" Med Sci Monit Basic Res., 19:93-102 (2013).
Jelovac, et al., "A novel pentadecapeptide, BPC 157, blocks the stereotypy produced acutely by amphetamine and the development of haloperidol-induced supersensitivity to amphetamine" Biol Psychiatry., 43(7):511-9 (1998).
Jelovac, et al., "Pentadecapeptide BPC 157 attenuates disturbances induced by neuroleptics: the effect on catalepsy and gastric ulcers in mice and rats" Eur J Pharmacol., 379(1):19-31 (1999b).
Jelovac, et al., "The effect of a novel pentadecapeptide BPC 157 on development of tolerance and physical dependence following repeated administration of diazepam" Chin J Physiol., 30;42 (3):171-9 (1999a).
Keremi, et al., "Antiinflammatory effect of BPC 157 on experimental periodontitis in rats" J Physiol Pharmacol., 60 Suppl 7:115-22 (2009).
Klicek, et al., "Pentadecapeptide BPC 157, in clinical trials as a therapy for inflammatory bowel disease (PL14736), is effective in the healing of colocutaneous fistulas in rats: role of the nitric oxide-system" J Pharmacol Sci., 108(1):7-17 (2008).
Klicek, et al., "Stable gastric pentadecapeptide BPC 157 heals cysteamine-colitis and colon-colon-anastomosis and counteracts cuprizone brain injuries and motor disability" J Physiol Pharmacol., 64(5):597-612 (2013).
Kokot, et al., "NO system dependence of atropine-induced mydriasis and L-NAME- and L-arginine-induced miosis: Reversal by the pentadecapeptide BPC 157 in rats and guinea pigs" Eur J Pharmacol., 771:211-9 (2016).
Krivic, et al., "Achilles detachment in rat and stable gastric pentadecapeptide BPC 157: Promoted tendon-to-bone healing and opposed corticosteroid aggravation" J Orthop Res. 24(5):982-9 (2006).
Lazic, et al., "Gastric pentadecapeptide BPC 157 promotes corneal epithelial defects healing in rats" Coll Antropol., 29(1):321-5 (2005).
LOVRIC-BENCIC1, et al., "Doxorubicine-congestive heart failure-increased big endothelin-1 plasma concentration: reversal by amlodipine, losartan, and gastric pentadecapeptide BPC157 in rat and mouse" J Pharmacol Sci., 95(1):19-26 (2004).
MacLaran, et al., "Managing low sexual desire in women" Womens Health (Lond)., 7(5):571-81 (2011).
Masnec, et al., "Perforating corneal injury in rat and pentadecapeptide BPC 157" Exp Eye Res. 136:9-15 (2015).
Mikus, et al., "Pentadecapeptide BPC 157 cream improves burn-wound healing and attenuates burn-gastric lesions in mice" Burns, 27(8):817-27 (2001).
Mise, et al., "The presentation and organization of adaptive cytoprotection in the rat stomach, duodenum, and colon. Dedicated to André Robert the founder of the concept of cytoprotection and adaptive cytoprotection" Med Sci Monit., 12(4):BR146-53 (2006).
Novinscak, et al., "Gastric pentadecapeptide BPC 157 as an effective therapy for muscle crush injury in the rat" Surg Today, 38(8):716-25 (2008).
Petek, et al., "Pentadecapeptide BPC 157 attenuates gastric lesions induced by alloxan in rats and mice" J Physiol Paris., 93(6):501-4 (1999).
Petrovic, et al., "An experimental model of prolonged esophagitis with sphincter failure in the rat and the therapeutic potential of gastric pentadecapeptide BPC 157" J Pharmacol Sci., 102(3):269-77 (2006).
Petrovic, et al., "BPC 157 therapy to detriment sphincters failure-esophagitis-pancreatitis in rat and acute pancreatitis patients low sphincters pressure" J Physiol Pharmacol., 62(5):527-34 (2011).
Pevec, et al., "Impact of pentadecapeptide BPC 157 on muscle healing impaired by systemic corticosteroid application" Med Sci Monit., 16(3):BR81-88 (2010).
Phillips, et al., "Depression and Sexual Desire" Am Fam Physician., 62(4):782-786 (2000).
Prkacin, et al., "Chronic cytoprotection: pentadecapeptide BPC 157, ranitidine and propranolol prevent, attenuate and reverse the gastric lesions appearance in chronic alcohol drinking rats" J Physiol Paris.,95(1-6):295-301 (2001a).
Prkacin, et al., "Portal hypertension and liver lesions in chronically alcohol drinking rats prevented and reversed by stable gastric pentadecapeptide BPC 157 (PL-10, PLD-116), and propranolol, but not ranitidine" J Physiol Paris., 95(1-6):315-24 (2001b).
Roa, et al., "Diagnosis and management of chronic constipation in adults" Nat Rev Gastroenterol Hepatol. 13(5):295-305. (2016).
Rotkvic, et al., "Inhibition and stimulation of prolactin release. Delayed response in duodenal ulcer patients" Dig Dis Sci., 37(12):1815-9 (1992).
Rucman, "New compound bepecin, process for its preparation, its use for the manufacture of pharmaceutical compositions and its use in therapy" Slovenian Patent Application, P-20100321 (2010).
Rucman, "Preparations with pentadekapeptidom BPC 157 , processes for their preparation and their use in cosmetics and dermatology" Slovenian Patent Application, P-20100322 (2010).
Sebecic, et al., "Osteogenic effect of a gastric pentadecapeptide, BPC-157, on the healing of segmental bone defect in rabbits: a comparison with bone marrow and autologous cortical bone implantation" Bone, 24(3):195-202 (1999).
Seiwerth, et al., "BPC 157's effect on healing" J Physiol Paris, 91(3-5):173-8 (1997).
Sever, et al., "Gastric pentadecapeptide BPC 157 and short bowel syndrome in rats" Dig Dis Sci., 54(10):2070-83 (2009).
Sikiric Editorial "How Drugs may Work to Better Protect the Gastrointestinal Tract" Current Pharmaceutical Design, vol. 19, No. 1, (2013).

(56) References Cited

OTHER PUBLICATIONS

Sikiric et al., "Brain-gut Axis and Pentadecapeptide BPC 157: Theroretical and Practical Implication" Current Neuropharmacology, 14, 857-865 (2016).
Sikiric et al., "The influence of dopamine agonists and antagonisits on gastric lesions in mice", European Journal of Pharmacology, 144 237-239, (1987).
Sikiric, "The pharmacological properties of the novel peptide BPC 157 (PL-10)" Inflammopharmacology,7(1):1-14 (1999a).
Sikiric, et al, "Hepatoprotective effect of BPC 157, a 15-amino acid peptide, on liver lesions induced by either restraint stress or bile duct and hepatic artery ligation or CCl4 administration. A comparative study with dopamine agonists and somatostatin" Life Sci., 53(18):PL291-6 (1993a).
Sikiric, et al, "New model of cytoprotection/adaptive cytoprotection in rats: endogenous small irritants, antiulcer agents and indomethacin" Eur J Pharmacol., 364(1):23-31 (1999b).
Sikiric, et al, "The beneficial effect of BPC 157, a 15 amino acid peptide BPC fragment, on gastric and duodenal lesions induced by restraint stress, cysteamine and 96% ethanol in rats. A comparative study with H2 receptor antagonists, dopamine promotors and gut peptides" Life Sci., 54(5):PL63-8 (1994).
Sikiric, et al, "The influence of a novel pentadecapeptide, BPC 157, on N(G)-nitro-L-arginine methylester and L-arginine effects on stomach mucosa integrity and blood pressure" Eur J Pharmacology 332(1):23-33 (1997a).
Sikiric, et al, "The influence of dopamine receptor agonists and an antagonist on acute pancreatitis in rats" Eur J Pharmacol., 147(3):321-326 (1988a).
Sikiric, et al., "A behavioural study of the effect of pentadecapeptide BPC 157 in Parkinson's disease models in mice and gastric lesions induced by 1-methyl-4-phenyl-1,2,3,6-tetrahydrophyridine" J Physiol Paris., 93(6):505-12 (1999c).
Sikiric, et al., "A new gastric juice peptide, BPC. An overview of the stomach-stress-organoprotection hypothesis and beneficial effects of BPC" J Physiol Paris., 87(5):313-27 (1993).
Sikiric, et al., "Anxiolytic effect of BPC-157, a gastric pentadecapeptide: shock probe/burying test and light/dark test" Acta Pharmacol Sin., 22(3):225-30 (2001a).
Sikiric, et al., "Beneficial effect of a novel pentadecapeptide BPC 157 on gastric lesions induced by restraint stress, ethanol, indomethacin, and capsaicin neurotoxicity" Dig Dis Sci., 41(8):1604-14 (1996a).
Sikiric, et al., "Corticosteroid-impairment of healing and gastric pentadecapeptide BPC-157 creams in burned mice" Burns, 29(4):323-34 (2003).
Sikiric, et al., "Cysteamine-colon and cysteamine-duodenum lesions in rats. Attenuation by gastric pentadecapeptide BPC 157, cimetidine, ranitidine, atropine, omeprazole, sulphasalazine and methylprednisolone" J Physiol Paris., 95(1-6):261-70 (2001b).
Sikiric, et al., "Dopamine agonists prevent duodenal ulcer relapse. A comparative study with famotidine and cimetidine" Dig Dis Sci., 36(7):905-10 (1991).
Sikiric, et al., "Dopamine antagonists induce gastric lesions in rats" Eur J Pharmacol., 12;131(1):105-9 (1986).
Sikiric, et al., "Emerging drugs in gastrointestinal tract" Curr Pharm Des., 17(16):1530-1 (2011a).
Sikiric, et al., "Focus on ulcerative colitis: stable gastric pentadecapeptide BPC 157" Curr Med Chem, 19(1):126-112) (2012).
Sikiric, et al., "Gastric mucosal lesions induced by complete dopamine system failure in rats. The effects of dopamine agents, ranitidine, atropine, omeprazole and pentadecapeptide BPC 157" J Physiol Paris., 94(2):105-10 (2000a).
Sikiric, et al., "Long-lasting cytoprotection after pentadecapeptide BPC 157, ranitidine, sucralfate or cholestyramine application in reflux oesophagitis in rats" J Physiol Paris., 93(6):467-77 (1999d).
Sikiric, et al., "Pentadecapeptide BPC 157 attenuates chronic amphetamine-induced behavior disturbances" Acta Pharmacol Sin., 23(5):412-22 (2002).
Sikiric, et al., "Pentadecapeptide BPC 157 positively affects both non-steroidal anti-inflammatory agent-induced gastrointestinal lesions and adjuvant arthritis in rats" J Physiology (Paris) 91(3-5):113-122 (1997c).
Sikiric, et al., "Pentadecapeptide BPC 157, cimetidine, ranitidine, bromocriptine, and atropine effect in cysteamine lesions in totally gastrectromized rats: a model for cytoprotective studies" Dig Dis Sci., 42(5):1029-37 (1997d).
Sikiric, et al., "Revised Robert's cytoprotection and adaptive cytoprotection and stable gastric pentadecapeptide BPC 157. Possible significance and implications for novel mediator" Curr Pharm Des., 16(10):1224-34 (2010).
Sikiric, et al., "Salutary and prophylactic effect of pentadecapeptide BPC 157 on acute pancreatitis and concomitant gastroduodenal lesions in rats" Dig Dis Sci., 41(7):1518-26 (1996b).
Sikiric, et al., "Stable gastric pentadecapeptide BPC 157 in trials for inflammatory bowel disease (PL-10, PLD-116, PL 14736, Pliva, Croatia). Full and distended stomach, and vascular response" Inflammopharmacology, 14(5-6):214-21 (2006).
Sikiric, et al., "Stable gastric pentadecapeptide BPC 157-NO-system relation" Curr Pharm Des., 20(7):1126-35 (2014).
Sikiric, et al., "Stable gastric pentadecapeptide BPC 157: novel therapy in gastrointestinal tract" Curr Pharm Des., 17(16):1612-32 (2011b).
Sikiric, et al., "Stress in gastrointestinal tract and stable gastric pentadecapeptide BPC 157. Finally, do we have a solution?" Curr Pharm Des., doi: 10.2174/1381612823666170220163219 (2017).
Sikiric, et al., "The antidepressant effect of an antiulcer pentadecapeptide BPC 157 in Porsolt's test and chronic unpredictable stress in rats. A comparison with antidepressants" J Physiol Paris., 94(2):99-104 (2000b).
Sikiric, et al., "The influence of dopamine agonists and antagonists on indomethacin lesions in stomach and small intestine in rats" Eur J Pharmacol, 158(1-2):61-67 (1988b).
Sikiric, et al., "The significance of the gastroprotective effect of body protection compound (BPC): modulation by different procedures" Acta Physiol Hung, 80(1-4):89-98 (1992).
Sikiric, et al., "Therapy effect of antiulcer agents on new chronic cysteamine colon lesion in rat" J Physiol Paris. 95(1-6):283-8 (2001c).
Sikiric, et al., "Toxicity by NSAIDs. Counteraction by stable gastric pentadecapeptide BPC 157" Curr Pharm Des., 19(1):76-83 (2013a).
Skorjanec, et al., "Duodenocutaneous fistula in rats as a model for "wound healing-therapy" in ulcer healing: the effect of pentadecapeptide BPC 157, L-nitro-arginine methyl ester and L-arginine" J Physiol Pharmacol., 66(4):581-90 (2015).
Skorjanec, et al., "Therapy for unhealed gastrocutaneous fistulas in rats as a model for analogous healing of persistent skin wounds and persistent gastric ulcers: stable gastric pentadecapeptide BPC 157, atropine, ranitidine, and omeprazole" Dig Dis Sci., 54(1):46-56 (2009).
Stambolija, et al., "BPC 157: The counteraction of succinylcholine, hyperkalemia, and arrhythmias" Eur J Pharmacol., 781:83-91 (2016).
Stancic-Rokotov, et al., "Ethanol gastric lesion aggravated by lung injury in rat. Therapy effect of antiulcer agents", J Physiol Paris., 95(1-6):289-93 (2001b).
Stancic-Rokotov, et al., "Lung lesions and anti-ulcer agents beneficial effect: anti-ulcer agents pentadecapeptide BPC 157, ranitidine, omeprazole and atropine ameliorate lung lesion in rats" J Physiol Paris. , 95(1-6):303-8 (2001a).
Staresinic, et al., "Effective therapy of transected quadriceps muscle in rat: Gastric pentadecapeptide BPC 157" J Orthop Res., 24(5):1109-17 (2006).
Staresinic, et al., "Gastric pentadecapeptide BPC 157 accelerates healing of transected rat Achilles tendon and in vitro stimulates tendocytes growth" J Orthop Res., 21(6):976-83 (2003).
Stupnisek, et al., "Pentadecapeptide BPC 157 Reduces Bleeding and Thrombocytopenia after Amputation in Rats Treated with Heparin, Warfarin, L-NAME and L-Arginine" PLoS One, 10(4):e0123454 (2015).
Stupnisek, et al., "Pentadecapeptide BPC 157 reduces bleeding time and thrombocytopenia after amputation in rats treated with heparin, warfarin or aspirin" Thromb Res., 129(5):652-9 (2012).

(56) References Cited

OTHER PUBLICATIONS

Tohoyama, et al., "Effects of pentadecapeptide BPC157 on regional serotonin synthesis in the rat brain: alpha-methyl-L-tryptophan autoradiographic measurements" Life Sci., 76(3):345-57 (2004).
Tudor, et al., "Traumatic brain injury in mice and pentadecapeptide BPC 157 effect" Regul Pept., 160(1-3):26-32 (2010).
Vuksic, et al., "Stable gastric pentadecapeptide BPC 157 in trials for inflammatory bowel disease (PL-10, PLD-116, PL14736, Pliva, Croatia) heals ileoileal anastomosis in the rat" Surg Today, 37(9):768-77 (2007).
Webster, et al., Opioid-induced constipation: rationale for the role of norbuprenorphine in buprenorphine-treated individuals Subst Abuse Rehabil., 7:81-6 (2016).

\* cited by examiner

SEQUENCE LISTING

```
<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 1

Gly Glu Pro Pro Pro Gly Lys Pro Ala Asp Asp Ala Gly Leu Val
1               5                   10                  15
```

COMPOSITIONS AND METHODS FOR TREATING SYMPTOMS ASSOCIATED WITH MULTIPLE SCLEROSIS

CROSS-REFERENCE TO RELATED APPLICATIONS

This application claims the benefit of and priority to U.S. Ser. No. 62/378,369, filed Aug. 23, 2016, and where permissible is hereby incorporated by reference in its entirety.

REFERENCE TO SEQUENCE LISTING

The Sequence Listing submitted as a text file named "PCD_100_ST25.txt," created on Aug. 2, 2017, and having a size of 550 bytes is hereby incorporated by reference.

FIELD OF THE INVENTION

The invention is generally directed to dosage forms of BPC (Body Protection Compound) peptide salts and methods of use.

BACKGROUND OF THE INVENTION

Multiple sclerosis (MS) is an autoimmune disorder of the central nervous system (CNS), and several factors are thought to influence an individual's susceptibility to the disease and the disease's course. In MS, the immune system—for reasons still not understood—attacks and destroys myelin and the oligodendrocytes that produce it. Eventually, there is a buildup of scar tissue (sclerosis) in multiple places where myelin has been lost; these plaques or scarred areas, which only are a fraction of an inch in diameter, can interfere with signal transmission. The underlying nerve also may be damaged, further worsening symptoms and reducing the degree of recovery. The disease can manifest itself in many ways. Sometimes the diseased areas cause no apparent symptoms, and sometimes they cause many; this is why the severity of problems varies greatly among people affected with MS. Multiple sclerosis usually strikes in the form of attacks or exacerbations. This is when at least one symptom occurs, or worsens, for more than 24 hours. The symptom(s) can last for days, weeks, months or indefinitely. MS is associated with pain. Bodily functions that are commonly affected include sexuality (diminished arousal and loss of sensation as well as bowel control, for example, constipation, etc.

It is an object of the present invention to provide compositions for treating one or more symptoms associated with MS.

It is also an object of the present invention to provide methods for treating one or more symptoms associated with MS.

SUMMARY OF THE INVENTION

Compositions and methods for treating one or more symptoms such as reduced sexual desire, fecal compaction and optionally, pain are provided. The compositions include unit dosage forms of pharmaceutically acceptable salts of a BPC peptide. The unit dosage forms can be formulated for enteral, parenteral, or topical administration. A preferred BPC free peptide is GEPPPGKPADDAGLV (SEQ ID NO:1) and the preferred salt is the sodium salt of BPC, more preferably, the disodium salt. The disclosed dosage forms and methods are based the discovery that BPC salts in addition to alleviating cramps associated with the menstrual cycle, can alleviate one or more symptoms such as reduced sexual desire and fecal compaction when administered in an effective amount and for an effective period of time. Accordingly, the disclosed composition can be administered to subjects in need thereof, for example patients with multiple sclerosis, especially patients whose MS symptoms are exacerbated in the premenstrual/menstrual time period.

Also provided herein are methods of increasing sexual desire or reducing fecal compaction in a subject in need thereof. In one embodiment, the compositions disclosed herein are used to alleviate one or more symptoms in patients with multiple sclerosis, particularly in patients in which multiple sclerosis symptoms are exacerbated in the premenstrual/menstrual time period. In another embodiment, the composition is administered to healthy subjects to increase sexual desire.

The disclosed dosage forms can be administered orally or parenterally.

DETAILED DESCRIPTION OF THE INVENTION

I. Definitions

The term "carrier" refers to a diluent, adjuvant, excipient, and/or vehicle with which the BPC salts are administered. The carrier is all components present in the pharmaceutical formulation other than the active ingredient or ingredients.

"Parenteral administration", as used herein, means administration by any method other than through the digestive tract or non-invasive topical or regional routes.

The term "pharmaceutically acceptable," as used herein with regard to pharmaceutical compositions, means approved by a regulatory agency of the Federal or a state government or listed in the U.S. Pharmacopeia or other generally recognized pharmacopeia for use in animals and/or in humans.

"Pharmaceutically acceptable salt", as used herein, refers to derivatives of the compounds defined herein, wherein the parent compound is modified by making acid or base salts thereof.

As used herein the term "effective amount" or "therapeutically effective amount" means a dosage sufficient to treat, inhibit, or alleviate one or more symptoms of the disorder being treated or to otherwise provide a desired pharmacologic and/or physiologic effect.

As used herein, "treatment" or "treating" refers to arresting, inhibiting, alleviating or attempting to arrest, inhibit, or alleviate one or more symptoms of the disorder being treated. As would be understood by those skilled in the art, various clinical and scientific methodologies and assays may be used to assess the development or progression of an infection, and similarly, various clinical and scientific methodologies and assays may be used to assess the reduction, regression, or remission of an infection or its symptoms.

As used herein, the term "subject" refers to an animal. Typically, the terms "subject" and "patient" may be used interchangeably herein in reference to a subject. As such, a "subject" includes a human that is being treated as a patient.

II. Compositions

The unit dosage forms disclosed herein include pharmaceutically acceptable salts of a BPC peptide. The unit dosage forms can be formulated for enteral, parenteral, or topical administration. The BPC peptide salt can be combined with one or more pharmaceutically acceptable carriers that are considered safe and effective to form a unit dosage as described herein, and may be administered to an individual without causing undesirable biological side effects or unwanted interactions.

These unit dosage forms can take the form of solutions, suspensions, emulsion, tablets, pills, capsules, powders, sustained-release formulations and the like.

In one preferred embodiment, the unit dosage form is in the form of a tablet, including a stabilized BPC peptide salt. The dosage form is administered to the subject in need thereof, for a time period effective to alleviate the desired symptom.

A. BPC Peptide Salts

The anion of the salt in a preferred embodiment is a negatively charged peptide including 8 to 15 amino acids with a molecular weight of 900 to 1,600 daltons and having the general formula (I): $X_1PPPX_2X_3PA](-)$ or (2–); $X_1$ can be, and is preferably a neutral aliphatic amino acid residue, for example, Ala, bAla, Leu, Ile, Gly, Val, Nle or Nva; $X_2$ can be, and is preferably a basic amino acid residue, for example Lys, Arg, Orn or His; and $X_3$ can be, and if preferably an acidic amino acid residue, for example, Glu, Asp, Aad or Apm.

The cation of the salt is preferably the cation of an inorganic or organic nontoxic and pharmaceutically acceptable base. In particular, the cation of the salt is an alkali metal or an alkaline earth metal, for instance $Na^+$, $K^+$, $Li^+$, $Cs^+$, $Ca^+$, or another metal, such as $Zn^{2+}$, or a primary, secondary or tertiary amine or organic compound, such as $NH_4^+$, triethanolamine$^+$, cyclohexylamine$^+$, 2-AMP$^+$ (2-amino-1-propanol) or TRIS$^+$ (Tris-(hydroxymethyl)-aminomethan). BPC peptide salts are disclosed in U.S. Pat. No. 6,288,028, the contents of which are herein incorporated by reference.

A preferred BPC free peptide is GEPPPGKPADDAGLV (SEQ ID NO:1) and a preferred salt is the sodium salt of BPC, preferably the disodium salt. The BPC salt in the formulations disclosed herein is preferably stabilized. Although many excipients have been disclosed in the art as useful in peptide formulations, obtaining a stabilized peptide formulation requires testing a combination of suitable excipients for the particular peptide. With peptides in particular one can obtain an undesirable effect and in fact reduce the stability of the peptide by merely selecting a generically disclosed excipient for inclusion into the peptide formulation. For example, reducing saccharides such as glucose can initiate unwanted degradation in peptide formulations. Lactose was shown to give rise to unwanted deposits in peptide formulations. See U.S. Publication No. 20070010424. U.S. Publication No. 20070010424 discloses problems with the use of a sugar alcohol such as mannitol in peptide formulations. For example, mannitol causes problems during the production of peptide formulations as it crystallizes resulting in deposits in the production equipment and in the final product when included in the peptide formulations at the low concentrations needed to use mannitol if selected as an isotonic agent. By contrast, and surprisingly, salts of BPC peptides disclosed herein can be stabilized with a sugar alcohol, preferably mannitol at concentrations up to a 1:1 ratio of BPC salt:sugar alcohol. A preferred stabilized BPC peptide salt includes mannitol in a 1:1 ratio mannitol:active agent; with the active agent, however, mannitol can be including a ratio ranging from 2:1 to a ratio of 1:2. The concentration of mannitol is effective to stabilize the formulation. For example, mannitol can make up between 40-70% by weight of the formulation, for example, 40%, 45%, 50%, 55%, 60%, 65% and 70%. Values intermediate to those specifically disclosed are also contemplated, for example, 61, 62, 63, 64, 65, 66, 67, 69, and 69%.

In this embodiment, the formulation preferably does not include an amphiphilic surfactant such as phospholipids or glycerophospholipids and/or propylene glycol.

B. Excipients and Carriers

Pharmaceutical carriers can be sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions.

Suitable pharmaceutical excipients include starch, glucose, sucrose, gelatin, lactose, malt, rice, flour, chalk, silica gel, sodium stearate, glycerol monostearate, talc, sodium chloride, glycerol, propylene, glycol, water, ethanol and the like. The pharmaceutical composition may also contain wetting or emulsifying agents or suspending/diluting agents, or pH buffering agents, or agents for modifying or maintaining the rate of release of the disclosed salts, all of which are disclosed further herein. Components of exemplary compositions including excipients are shown in Table 1.

TABLE 1

Composition of BPC peptide formulation

| Agent | Concentration (mg) |
| --- | --- |
| Active Pharmaceutical Ingredient | 2.0 |
| Mannitol-PARTECK ® | 69.7 |
| Cellulose-AVICEL ® | 25.3 |
| Sodium hydrogen carbonate | 1.3 |
| Silicon dioxide-AEROSIL ® | 0.7 |
| Magnesium stearate | 1.0 |
| Total | 100 |

C. Dosage Forms

The dosage forms include parenteral and enteral dosage forms. BPC peptide salts are preferably present in the dosage forms in an amount ranging from 1 to 10 mg/dosage form, for example, 1 mg, 2 mg, 3 mg, 4 mg, 5 mg, 6 mg, 7 mg, 8 mg, 9 mg or 10 mg. For example, an enteric tablet from can include 1 mg, 2 mg, 3 mg, 4 mg, 5 mg, 6 mg, 7 mg, 8 mg, 9 mg or 10 mg of the BPC peptide salt.

1. Parenteral Formulations

The BPC salts described herein can be formulated for parenteral administration. Parenteral administration may include administration to a patient intravenously, intradermally, intraarterially, intraperitoneally, intralesionally, intraarticularly, intraprostatically, intrapleurally, intratracheally, intratumorally, intramuscularly, subcutaneously, subconjunctivally, intravesicularly, intrapericardially, intraumbilically, by injection, and by infusion.

Parenteral formulations can be prepared as aqueous compositions using techniques known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

If for intravenous administration, the compositions are packaged in solutions of sterile isotonic aqueous buffer. Where necessary, the composition may also include a solubilizing agent. The components of the composition are can be either separately or mixed together in unit dosage form, for example, as a dry lyophilized powder (which can be reconstituted before use with a carrier such as saline) or concentrated solution in a hermetically sealed container such as an ampoule or sachet indicating the amount of active agent. If the composition is to be administered by infusion, it can be dispensed with an infusion bottle containing sterile pharmaceutical grade water or saline. Where the composition is administered by injection, an ampoule of sterile water or saline can be provided so that the ingredients may be mixed prior to injection.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, viscosity modifying agents, and combination thereof.

Suitable surfactants may be anionic, cationic, amphoteric or nonionic surface-active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene, and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-laurylβiminodipropionate, myristoamphoacetate, lauryl betaine, and lauryl sulfobetaine. The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water-soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

(a) Controlled Release Formulations

The parenteral formulations described herein can be formulated for controlled release including immediate release, delayed release, extended release, pulsatile release, and combinations thereof.

1. Nano- and Microparticles

For parenteral administration, the one or more compounds, and optional one or more additional active agents, can be incorporated into microparticles, nanoparticles, or combinations thereof that provide controlled release of the compounds and/or one or more additional active agents. In forms wherein the formulations contains two or more drugs, the drugs can be formulated for the same type of controlled release (e.g., delayed, extended, immediate, or pulsatile) or the drugs can be independently formulated for different types of release (e.g., immediate and delayed, immediate and extended, delayed and extended, delayed and pulsatile, etc.).

For example, the compounds and/or one or more additional active agents can be incorporated into polymeric microparticles, which provide controlled release of the drug(s). Release of the drug(s) is controlled by diffusion of the drug(s) out of the microparticles and/or degradation of the polymeric particles by hydrolysis and/or enzymatic degradation. Suitable polymers include ethylcellulose and other natural or synthetic cellulose derivatives.

Polymers, which are slowly soluble and form a gel in an aqueous environment, such as hydroxypropyl methylcellulose or polyethylene oxide, can also be suitable as materials for drug containing microparticles. Other polymers include, but are not limited to, polyanhydrides, poly(ester anhydrides), polyhydroxy acids, such as polylactide (PLA), polyglycolide (PGA), poly(lactide-co-glycolide) (PLGA), poly-3-hydroxybutyrate (PHB) and copolymers thereof, poly-4-hydroxybutyrate (P4HB) and copolymers thereof, polycaprolactone and copolymers thereof, and combinations thereof.

Alternatively, the drug(s) can be incorporated into microparticles prepared from materials which are insoluble in aqueous solution or slowly soluble in aqueous solution, but are capable of degrading within the GI tract by means including enzymatic degradation, surfactant action of bile acids, and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including but not limited to fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes. Specific examples of waxes include beeswax, glycowax, castor wax, carnauba wax, paraffins and candelilla wax. As used herein, a wax-like material is defined as any material, which is normally solid at room temperature and has a melting point of from about 30 to 300° C.

In some cases, it may be desirable to alter the rate of water penetration into the microparticles. To this end, rate-controlling (wicking) agents can be formulated along with the fats or waxes listed above. Examples of rate-controlling materials include certain starch derivatives (e.g., waxy maltodextrin and drum dried corn starch), cellulose derivatives (e.g., hydroxypropylmethylcellulose, hydroxypropylcellulose, methylcellulose, and carboxymethylcellulose), alginic acid, lactose and talc. Additionally, a pharmaceutically acceptable surfactant (for example, lecithin) may be added to facilitate the degradation of such microparticles.

Proteins, which are water insoluble, such as zein, can also be used as materials for the formation of drug containing microparticles. Additionally, proteins, polysaccharides and combinations thereof, which are water-soluble, can be formulated with drug into microparticles and subsequently cross-linked to form an insoluble network. For example, cyclodextrins can be complexed with individual drug molecules and subsequently cross-linked.

2. Method of Making Nano- and Microparticles

Encapsulation or incorporation of drug into carrier materials to produce drug-containing microparticles can be achieved through known pharmaceutical formulation techniques. In the case of formulation in fats, waxes or wax-like materials, the carrier material is typically heated above its melting temperature and the drug is added to form a mixture comprising drug particles suspended in the carrier material, drug dissolved in the carrier material, or a mixture thereof. Microparticles can be subsequently formulated through several methods including, but not limited to, the processes of congealing, extrusion, spray chilling or aqueous dispersion. In a preferred process, wax is heated above its melting temperature, drug is added, and the molten wax-drug mixture is congealed under constant stirring as the mixture cools. Alternatively, the molten wax-drug mixture can be extruded and spheronized to form pellets or beads. These processes are known in the art.

For some carrier materials it may be desirable to use a solvent evaporation technique to produce drug-containing microparticles. In this case drug and carrier material are co-dissolved in a mutual solvent and microparticles can subsequently be produced by several techniques including, but not limited to, forming an emulsion in water or other appropriate media, spray drying or by evaporating off the solvent from the bulk solution and milling the resulting material.

In some forms, drug in a particulate form is homogeneously dispersed in a water-insoluble or slowly water soluble material. To minimize the size of the drug particles within the composition, the drug powder itself may be milled to generate fine particles prior to formulation. The process of jet milling, known in the pharmaceutical art, can be used for this purpose. In some forms, drug in a particulate form is homogeneously dispersed in a wax or wax like substance by heating the wax or wax like substance above its melting point and adding the drug particles while stirring the mixture. In this case a pharmaceutically acceptable surfactant may be added to the mixture to facilitate the dispersion of the drug particles.

The particles can also be coated with one or more modified release coatings. Solid esters of fatty acids, which are hydrolyzed by lipases, can be spray coated onto microparticles or drug particles. Zein is an example of a naturally water-insoluble protein. It can be coated onto drug containing microparticles or drug particles by spray coating or by wet granulation techniques. In addition to naturally water-insoluble materials, some substrates of digestive enzymes can be treated with cross-linking procedures, resulting in the formation of non-soluble networks. Many methods of cross-linking proteins, initiated by both chemical and physical means, have been reported. One of the most common methods to obtain cross-linking is the use of chemical cross-linking agents. Examples of chemical cross-linking agents include aldehydes (gluteraldehyde and formaldehyde), epoxy compounds, carbodiimides, and genipin. In addition to these cross-linking agents, oxidized and native sugars have been used to cross-link gelatin. Cross-linking can also be accomplished using enzymatic means; for example, transglutaminase has been approved as a GRAS substance for cross-linking seafood products. Finally, cross-linking can be initiated by physical means such as thermal treatment, UV irradiation and gamma irradiation.

To produce a coating layer of cross-linked protein surrounding drug containing microparticles or drug particles, a water-soluble protein can be spray coated onto the microparticles and subsequently cross-linked by the one of the methods described above. Alternatively, drug-containing microparticles can be microencapsulated within protein by coacervation-phase separation (for example, by the addition of salts) and subsequently cross-linked. Some suitable proteins for this purpose include gelatin, albumin, casein, and gluten.

Polysaccharides can also be cross-linked to form a water-insoluble network. For many polysaccharides, this can be accomplished by reaction with calcium salts or multivalent cations, which cross-link the main polymer chains. Pectin, alginate, dextran, amylose and guar gum are subject to cross-linking in the presence of multivalent cations. Complexes between oppositely charged polysaccharides can also be formed; pectin and chitosan, for example, can be complexed via electrostatic interactions.

(b) Injectable/Implantable Formulations

The compounds described herein can be incorporated into injectable/implantable solid or semi-solid implants, such as polymeric implants. In some forms, the compounds are incorporated into a polymer that is a liquid or paste at room temperature, but upon contact with aqueous medium, such as physiological fluids, exhibits an increase in viscosity to form a semi-solid or solid material. Exemplary polymers include, but are not limited to, hydroxyalkanoic acid polyesters derived from the copolymerization of at least one unsaturated hydroxy fatty acid copolymerized with hydroxyalkanoic acids. The polymer can be melted, mixed with the active substance and cast or injection molded into a device. Such melt fabrication requires polymers having a melting point that is below the temperature at which the substance to be delivered and polymer degrade or become reactive. The device can also be prepared by solvent casting where the polymer is dissolved in a solvent and the drug dissolved or dispersed in the polymer solution and the solvent is then evaporated. Solvent processes require that the polymer be soluble in organic solvents. Another method is compression molding of a mixed powder of the polymer and the drug or polymer particles loaded with the active agent.

Alternatively, the compounds can be incorporated into a polymer matrix and molded, compressed, or extruded into a device that is a solid at room temperature. For example, the compounds can be incorporated into a biodegradable polymer, such as polyanhydrides, polyhydroalkanoic acids (PHAs), PLA, PGA, PLGA, polycaprolactone, polyesters, polyamides, polyorthoesters, polyphosphazenes, proteins and polysaccharides such as collagen, hyaluronic acid, albumin and gelatin, and combinations thereof and compressed into solid device, such as disks, or extruded into a device, such as rods.

The release of the one or more compounds from the implant can be varied by selection of the polymer, the molecular weight of the polymer, and/or modification of the polymer to increase degradation, such as the formation of pores and/or incorporation of hydrolyzable linkages. Methods for modifying the properties of biodegradable polymers to vary the release profile of the compounds from the implant are well known in the art.

2. Enteral Formulations

Oral formulations can include standard carriers such as pharmaceutical grades of mannitol, lactose, sodium saccharine, starch, magnesium stearate, cellulose, magnesium carbonate, etc. Such compositions will contain a therapeutically effective amount of the disclosed salts with a suitable amount of carrier so as to provide the proper form to the patient based on the mode of administration to be used.

Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art. The preferred formulation is a tablet, preferably including mannitol in a 1:1 ratio mannitol:active agent; with the active agent, however, mannitol can be including a ratio ranging from 2:1 to a ratio of 1:2. The concentration of mannitol is effective to stabilize the formulation. For example, mannitol can make up between 40-70% by weight of the formulation, for example, 40%, 45%, 50%, 55%, 60%, 65% and 70%. Values intermediate to those specifically disclosed are also contemplated, for example, 61, 62, 63, 64, 65, 66, 67, 69, and 69%. Preferred formulations include microcyrstalline cellulose at a concentration ranging from 10-30% w/w preferably, between 15 and 26% w/w.

Formulations may be prepared using a pharmaceutically acceptable carrier. As generally used herein "carrier" includes, but is not limited to, diluents, preservatives, binders, lubricants, disintegrators, swelling agents, fillers, stabilizers, and combinations thereof.

Carrier also includes all components of the coating composition, which may include plasticizers, pigments, colorants, stabilizing agents, and glidants. Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

"Diluents", also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

"Binders" are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, AVCEL® (microcrystalline cellulose), ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

"Lubricants" are used to facilitate tablet manufacture. Examples of suitable lubricants include, but are not limited to, magnesium stearate, calcium stearate, stearic acid, glycerol behenate, polyethylene glycol, talc, and mineral oil, including in a concentration range between 0.5 and 2.6% w/w of the formulation, preferably, between 1 and 2.0%.

"Disintegrants" are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

"Stabilizers" are used to inhibit or retard drug decomposition reactions, which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

(a) Controlled Release Enteral Formulations

Oral dosage forms, such as capsules, tablets, solutions, and suspensions, can for formulated for controlled release. For example, the one or more compounds and optional one or more additional active agents can be formulated into nanoparticles, microparticles, and combinations thereof, and encapsulated in a soft or hard gelatin or non-gelatin capsule or dispersed in a dispersing medium to form an oral suspension or syrup. The particles can be formed of the drug and a controlled release polymer or matrix. Alternatively, the drug particles can be coated with one or more controlled release coatings prior to incorporation in to the finished dosage form.

In another form, the one or more compounds and optional one or more additional active agents are dispersed in a matrix material, which gels or emulsifies upon contact with an aqueous medium, such as physiological fluids. In the case of gels, the matrix swells entrapping the active agents, which are released slowly over time by diffusion and/or degradation of the matrix material. Such matrices can be formulated as tablets or as fill materials for hard and soft capsules.

In still another form, the one or more compounds, and optional one or more additional active agents are formulated into a sold oral dosage form, such as a tablet or capsule, and the solid dosage form is coated with one or more controlled release coatings, such as a delayed release coatings or extended release coatings. The coating or coatings may also contain the compounds and/or additional active agents.

(1) Extended Release Dosage Forms

The extended release formulations are generally prepared as diffusion or osmotic systems, which are known in the art. A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof. In certain preferred forms, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred forms, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred form, the acrylic polymer is an acrylic resin lacquer such as that which is commercially available from Rohm Pharma under the tradename EUDRAGIT®. In further preferred forms, the acrylic polymer comprises a mixture of two acrylic resin lacquers commercially available from Rohm Pharma under the tradenames EUDRAGIT® RL30D and EUDRAGIT® RS30D, respectively. EUDRAGIT® RL30D and EUDRAGIT® RS30D are copolymers of acrylic and methacrylic esters with a low content of quaternary ammonium groups, the molar ratio of ammonium groups to the remaining neutral (meth)acrylic esters being 1:20 in EUDRAGIT® RL30D and 1:40 in EUDRAGIT® RS30D. The mean molecular weight is about 150,000. EUDRAGIT® S-100 and EUDRAGIT® L-100 are also preferred. The code designations RL (high permeability) and RS (low permeability) refer to the permeability properties of these agents. EUDRAGIT® RL/RS mixtures are insoluble in water and in digestive fluids. However, multiparticulate systems formed to include the same are swellable and permeable in aqueous solutions and digestive fluids.

The polymers described above such as EUDRAGIT® RL/RS may be mixed together in any desired ratio in order to ultimately obtain a sustained-release formulation having a desirable dissolution profile. Desirable sustained-release multiparticulate systems may be obtained, for instance, from 100% EUDRAGIT® RL, 50% EUDRAGIT® RL and 50% EUDRAGIT t® RS, and 10% EUDRAGIT® RL and 90% EUDRAGIT® RS. One skilled in the art will recognize that other acrylic polymers may also be used, such as, for example, EUDRAGIT® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion. The devices with different drug release mechanisms described above can be combined in a final dosage form comprising single or multiple units. Examples of multiple units include, but are not limited to, multilayer tablets and capsules containing tablets, beads, or granules An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

(2) Delayed Release Dosage Forms

Delayed release formulations can be created by coating a solid dosage form with a polymer film, which is insoluble in the acidic environment of the stomach, and soluble in the neutral environment of the small intestine. The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including EUDRAGIT® L30D-55 and L100-55 (soluble at pH 5.5 and above), EUDRAGIT® L-100 (soluble at pH 6.0 and above), EUDRAGIT® S (soluble at pH 7.0 and above, as a result of a higher degree of esterification), and EUDRAGITS® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

3. Topical Formulations

Suitable dosage forms for topical administration include creams, ointments, salves, sprays, gels, lotions, emulsions, and transdermal patches. The formulation may be formulated for transmucosal, transepithelial, transendothelial, or transdermal administration. The compounds can also be formulated for intranasal delivery, pulmonary delivery, or inhalation. The compositions may further contain one or more chemical penetration enhancers, membrane permeability agents, membrane transport agents, emollients, surfactants, stabilizers, buffers, and combination thereof.

In certain forms, it may be desirable to provide continuous delivery of one or more compounds to a patient in need thereof. For topical applications, repeated application can be done or a patch can be used to provide continuous administration of the compounds over an extended period of time "Buffers" are used to control pH of a composition. Preferably, the buffers buffer the composition from a pH of about 4 to a pH of about 7.5, more preferably from a pH of about 4 to a pH of about 7, and most preferably from a pH of about 5 to a pH of about 7. In a preferred form, the buffer is triethanolamine.

"Emollients" are an externally applied agent that softens or soothes skin and are generally known in the art and listed in compendia, such as the "Handbook of Pharmaceutical Excipients", $4^{th}$ Ed., Pharmaceutical Press, 2003. These include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In some forms, the emollients are ethylhexylstearate and ethylhexyl palmitate.

"Emulsifiers" are surface active substances which promote the suspension of one liquid in another and promote the formation of a stable mixture, or emulsion, of oil and water. Common emulsifiers are: metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxypropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In some forms, the emulsifier is glycerol stearate.

"Penetration enhancers" are known in the art and include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocylic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols). Examples of these classes are known in the art.

"Preservatives" can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

"Surfactants" are surface-active agents that lower surface tension and thereby increase the emulsifying, foaming, dispersing, spreading and wetting properties of a product. Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In some forms, the non-ionic surfactant is stearyl alcohol.

(a) Emulsions

An emulsion is a preparation of one liquid distributed in small globules throughout the body of a second liquid. In particular forms, the non-miscible components of the emulsion include a lipophilic component and an aqueous component. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

The oil phase may consist at least in part of a propellant, such as an HFA propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

A sub-set of emulsions are the self-emulsifying systems. These drug delivery systems are typically capsules (hard shell or soft shell) comprised of the drug dispersed or dissolved in a mixture of surfactant(s) and lipophilic liquids such as oils or other water immiscible liquids. When the capsule is exposed to an aqueous environment and the outer gelatin shell dissolves, contact between the aqueous medium and the capsule contents instantly generates very small emulsion droplets. These typically are in the size range of micelles or nanoparticles. No mixing force is required to generate the emulsion as is typically the case in emulsion formulation processes.

(b) Lotions

A lotion can contain finely powdered substances that are in soluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In some forms, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

(c) Creams

Creams may contain emulsifying agents and/or other stabilizing agents. In some forms, the formulation is in the form of a cream having a viscosity of greater than 1000 centistokes, typically in the range of 20,000-50,000 centistokes. Creams are often time preferred over ointments, as they are generally easier to spread and easier to remove.

The difference between a cream and a lotion is the viscosity, which is dependent on the amount/use of various oils and the percentage of water used to prepare the formulations. Creams are typically thicker than lotions, may have various uses and often one uses more varied oils/butters, depending upon the desired effect upon the skin. In a cream formulation, the water-base percentage is about 60-75% and the oil-base is about 20-30% of the total, with the other percentages being the emulsifier agent, preservatives and additives for a total of 100%.

III. Methods of Use

Preferably, the subjects disclosed herein receive the dosage formulations for an effective amount of time to obtain the desired relief from the symptom being treated. For example, the dosage forms are administered once a day for at least one week, preferably, at least two weeks, and more preferably, least twice a day for at least two weeks. For example, the subjects can receive a 3 mg dosage form two times a day for at least two weeks, to alleviate one or more symptoms.

In one embodiment, the dosage form is administered to a subject in need thereof to treat a condition/symptom associated with the menstrual cycle, for example, pain, and/or MS flaring in association with the menstrual cycle. In a study published in 2002, 42% MS patients had exacerbations starting in the premenstrual phase. Within this group the proportion of premenstrual exacerbations was significantly higher than in the remaining period of the menstrual cycle, and in 45% all exacerbations had started during the premenstrual phase. There was no relationship with the premenstrual syndrome, and there was no protective effect of oral contraceptives. Zorgdrager, et al., *Eur Neurol.,* 2002; 48:204-206. Another study showed worsening of symptoms in 42% of the patients studied, during menses (Avila, et al., "Menstrual Cycle, menopause and pregnancy in patients with multiple sclerosis. How these affect the symptoms of disease?"). Exemplary symptoms that can be alleviated in MS patients include pain, fecal compaction and/or reduced sexual desire, when compared to the same symptoms in the same subject not receiving the disclosed compositions.

In another embodiment, the dosage form is administered to a subject to enhance sexual desire in subjects with Hypoactive Sexual Desire Disorder, loss of sexual desire, lack of sexual desire, decreased sexual desire, inhibited sexual desire, loss of libido, libido disturbance, and frigidity ("collectively, sexual desire disorders) or in healthy subject who do not show any loss or decrease in sexual desire i.e., who do not have a sexual desire disorder, but who desire to enhance sexual desire. In this embodiment, the subject preferably does not present with erectile dysfunction. Erectile dysfunction (ED) is defined by the National Institutes of Health as the inability to achieve or maintain an erection sufficient for satisfactory sexual performance (Impotence. *NIH Consens Statement.* 1992; 10(4):1-33). Low sexual desire is a common problem amongst men and women. When associated with distress, it is termed hypoactive sexual desire disorder (HSDD), which is estimated to affect approximately one in ten women. The prevalence of low sexual desire increases with age, which partly reflects the normal aging process but is also caused by the effect of the menopause on sexual function. In a national survey conducted in 1994, 33 percent of women and 17 percent of men reported sexual disinterest. In another survey, one third of women 18 to 59 years of age reported feeling a lack of sexual desire within the previous year; these statistics increase within the context of depression (Reviewed in Phillips, et al., *Am Fam Physician.* 2000 Aug. 15; 62(4): 782-786). Hypoactive sexual desire disorder is currently defined by The American Psychiatric Association's Diagnostic and Statistical Manual of Mental Disorders 4 (DSM-IV) as a persistent or recurrent deficiency or absence of sexual fantasies and desire for sexual activity that causes marked distress or interpersonal difficulty. The World Health Organization also classifies low sexual desire with similar criteria (reviewed in Maclaran, et al., *Womens Health* (Lond). 2011 September; 7(5):571-81.

In another embodiment, the dosage form is administered to a subject in need of stool loosening, for example, a subject with constipation, preferably, chronic constipation. Constipation as used herein refers to bowel movements that are infrequent (typically three times or fewer per week) or hard to pass. Constipation is a heterogeneous, polysymptomatic, multifactorial disease. Acute or transient constipation can be due to changes in diet, travel or stress, and secondary constipation can result from drug treatment, neurological or metabolic conditions or, rarely, colon cancer. Severe constipation includes obstipation (failure to pass stools or gas) and fecal impaction, which can progress to bowel obstruction and become life-threatening. Constipation can be caused by obstructed defecation or colonic slow transit (or hypomobility). Causes of colonic slow transit constipation include diet, hormonal disorders such as hypothyroidism, side effects of medications, and in very rare instances, heavy metal toxicity. A diagnosis of primary chronic constipation is made after exclusion of secondary causes of constipation and encompasses several overlapping subtypes. Slow-transit constipation is characterized by prolonged colonic transit in the absence of pelvic floor dysfunction. This subtype of constipation can be identified using either the radio-opaque marker test or wireless motility capsule test, and is best treated with laxatives such as polyethylene glycol or newer agents such as linaclotide or lubiprostone. If unsuccessful, subspecialist referral should be considered. Dyssynergic defecation results from impaired coordination of rectoanal and pelvic floor muscles, and causes difficulty with defecation. The condition can be identified using anorectal manometry and balloon expulsion tests and is best managed with biofeedback therapy. Roa, et al., *Nat Rev Gastroenterol Hepatol.* 13(5):295-305. (2016). Medications which have been associated with constipation as a side effect include, but are not limited to, opioids, for example Buprenorphine and buprenorphine, diuretics, antidepressants, antihistamines, antispasmodics, anticonvulsants, and aluminum antacids, and calcium channel blockers such as nifedipine and verapamil. Webster, et al., Subst Abuse Rehabil. 2016; 7: 81-86. Accordingly, co-administration of the dosage forms disclosed herein with these medications can alleviate at least one symptom associated with constipation, for example, In still another embodiment, the dosage form is administered to a patient in need of relief from pain associated with chronic cevicalgia.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

I claim:

1. A unit dosage form composition for oral administration or in the form of a transdermal patch comprising a stabilized Body Protection Compound Peptide (BPC) having the sequence GEPPPGKPADDAGLV (SEQ ID NO:1), stabilized with a salt and a sugar alcohol having enhanced stability of the BPC salt as compared to the BPC salt not formulated with the sugar alcohol.

2. The composition of claim 1 in the form of a solution, suspension, emulsion, tablets, capsules or powder for oral administration.

3. The composition of claim 1 in the form of a transdermal patch.

4. The composition of claim 2 in the form of a kit comprising a reconstitutable powder and excipient for reconstitution.

5. The composition of any of claim 1, wherein the % by weight of the unit dosage ratio of BPC salt:sugar alcohol is between 2:1 and 1:2.

6. The composition of claim 5, wherein the % by weight of the unit dosage ratio of BPC salt:sugar alcohol is 1:1.

7. The composition of claim 5, wherein the sugar alcohol is mannitol present in a concentration between 40 and 70% by weight of the unit dosage form.

8. The composition form of claim 7, wherein mannitol is present in a concentration between 45 and 55% by weight of the unit dosage form.

9. The unit dosage form of claim 5, wherein the sugar alcohol is mannitol wherein mannitol is present in a concentration of about 70% by weight of the unit dosage.

10. A method for treating one or more symptoms of an individual in need thereof selected from the group consisting of individuals suffering from impotence, gastrointestinal disorders, and, pain comprising administering orally or transdermally to a subject in need thereof a unit dosage form composition comprising a therapeutically effective amount of a stabilized Body Protection Compound Peptide (BPC) having the sequence GEPPPGKPADDAGLV (SEQ ID NO:1), stabilized with a salt and a sugar alcohol having enhanced stability of the BPC salt as compared to the BPC salt not formulated with the sugar alcohol.

11. The method of claim 10, wherein the composition is administered orally.

12. The method of claim 10, wherein the BPC salt is a sodium salt of GEPPPGKPADDAGLV (SEQ ID NO:1).

13. The method of claim 11, wherein the composition is a tablet, comprising mannitol in a concentration between 45 and 55% by weight of the unit dosage form.

14. The method of claim 11, wherein the composition is a tablet, comprising mannitol in a concentration about 70% by weight of the unit dosage form.

15. The method of claim 13, wherein the composition is administered once a day for at least one week.

16. The method of claim 15, wherein the composition is administered to the subject for at least two weeks.

17. The method of claim 16, wherein the subjected is administered 1, 3, 6 or 9 mg of the BPC salt.

18. The method of any one of claim 10 wherein the subject has a conditions selected from the group consisting of cervicalgia, constipation, Multiple sclerosis (MS), menstrual cramps, Hypoactive Sexual Desire Disorder, loss of sexual desire, lack of sexual desire, decreased sexual desire, inhibited sexual desire, loss of libido, libido disturbance, frigidity.

19. The method of claim 18 wherein the subject's MS symptoms are exacerbated in the premenstrual time period/during the menstrual period.

20. The method of claim 10, wherein the dosage unit is a transdermal patch.

* * * * *